United States Patent [19]

Caputo et al.

[11] Patent Number: 5,498,526

[45] Date of Patent: Mar. 12, 1996

[54] BACILLUS CIRCULANS BASED BIOLOGICAL INDICATOR FOR GASEOUS STERILANTS

[75] Inventors: Ross A. Caputo, Long Grove, Ill.; Phillip A. Martens, Fremont, Calif.

[73] Assignee: Abtox, Inc., Mundelein, Ill.

[21] Appl. No.: 111,989

[22] Filed: Aug. 25, 1993

[51] Int. Cl.$^6$ .............................. C12Q 1/02; C12Q 1/22
[52] U.S. Cl. ........................ 435/31; 435/242; 435/832; 435/835; 315/111.21; 422/58; 422/61; 436/1; 436/163
[58] Field of Search ............................ 435/31, 242, 291, 435/832, 835; 315/111.21; 250/282; 356/246; 422/58, 61; 436/1, 163

[56] References Cited

U.S. PATENT DOCUMENTS

| | | | |
|---|---|---|---|
| 3,346,464 | 10/1967 | Ernst | 435/31 |
| 3,440,144 | 4/1969 | Andersen | 435/31 |
| 3,661,717 | 5/1972 | Nelson | 435/31 |
| 4,717,661 | 6/1988 | McCormick et al. | 435/31 |
| 4,743,537 | 5/1988 | McCormick et al. | 435/296 |
| 4,828,797 | 5/1989 | Zwarun et al. | 422/55 |
| 4,914,034 | 4/1990 | Welsh et al. | 435/296 |
| 4,937,115 | 6/1990 | Leatherman | 428/364 |
| 5,084,239 | 1/1992 | Moulton et al. | 422/22 |
| 5,115,166 | 5/1992 | Campbell et al. | 315/111.21 |
| 5,270,650 | 12/1993 | Schenz et al. | 324/308 |

OTHER PUBLICATIONS

Davenport Journal of Parenteral Science & Technology vol. 43, No. 4 pp. 158–166 (1989).
"Biological Indicator for Dry–Heat Sterilization, Paper Strip," *U.S. Pharmacopeia XXII, Official Monograph*, pp. 170–171. (1990).
Davenport, "Design and Use of a Novel Peracetic Acid Sterilizer for Absolute Barrier Sterility Testing Chambers," *Journal of Parenteral Science & Technology*, 43(4), 1989, pp. 158–166.
Macek, "Biological Indicators—A U.S.P. Review," *Bulletin of the Parenteral Drug Association*, 26(1), 1972, pp. 18–25.
"Biological Indicators," *U.S. Pharmacopeia XXII, Official Monograph*, pp. 1625–1626. (1990).
Code of Federal Regulations, Title 21: Food and Drug Administration, Department of Health and Human Services, Subchapter H—Medical Devices, Part 880.2800, pp. 322–323. (1990).
"Biological Indicator for Steam Sterilization, Paper Strip" *U.S. Pharmacopeia XXII, Official Monograph*, pp. 173–175. (1990).
"Biological Indicator for Ethylene Oxide Sterilization, Paper Strip" *U.S. Pharmacopeia XXII, Official Monograph*, pp. 171–175. (1990).
Premarket Notification to Food and Drug Administration, Jul. 24, 1992.
Miyauchi et al., "Microbiological Studies on Heat Processed Foods: 1. Survival of Microorganisms in Commercial Canned Foods," *Biological Abstracts*, 72:5, abstract No. 30742 (1981).

Primary Examiner—Michael G. Wityshyn
Assistant Examiner—Jane A. Williams
Attorney, Agent, or Firm—Majestic, Parsons, Siebert & Hsue

[57] ABSTRACT

Biological indicators are provided for use in validating and routinely monitoring oxidizing gas sterilizations. The biological indicators are based on *Bacillus circulans* spores that are enclosed in packages with sufficient permeability to admit a sterilizing amount of vapor while being substantially bacteria impermeable.

13 Claims, 3 Drawing Sheets

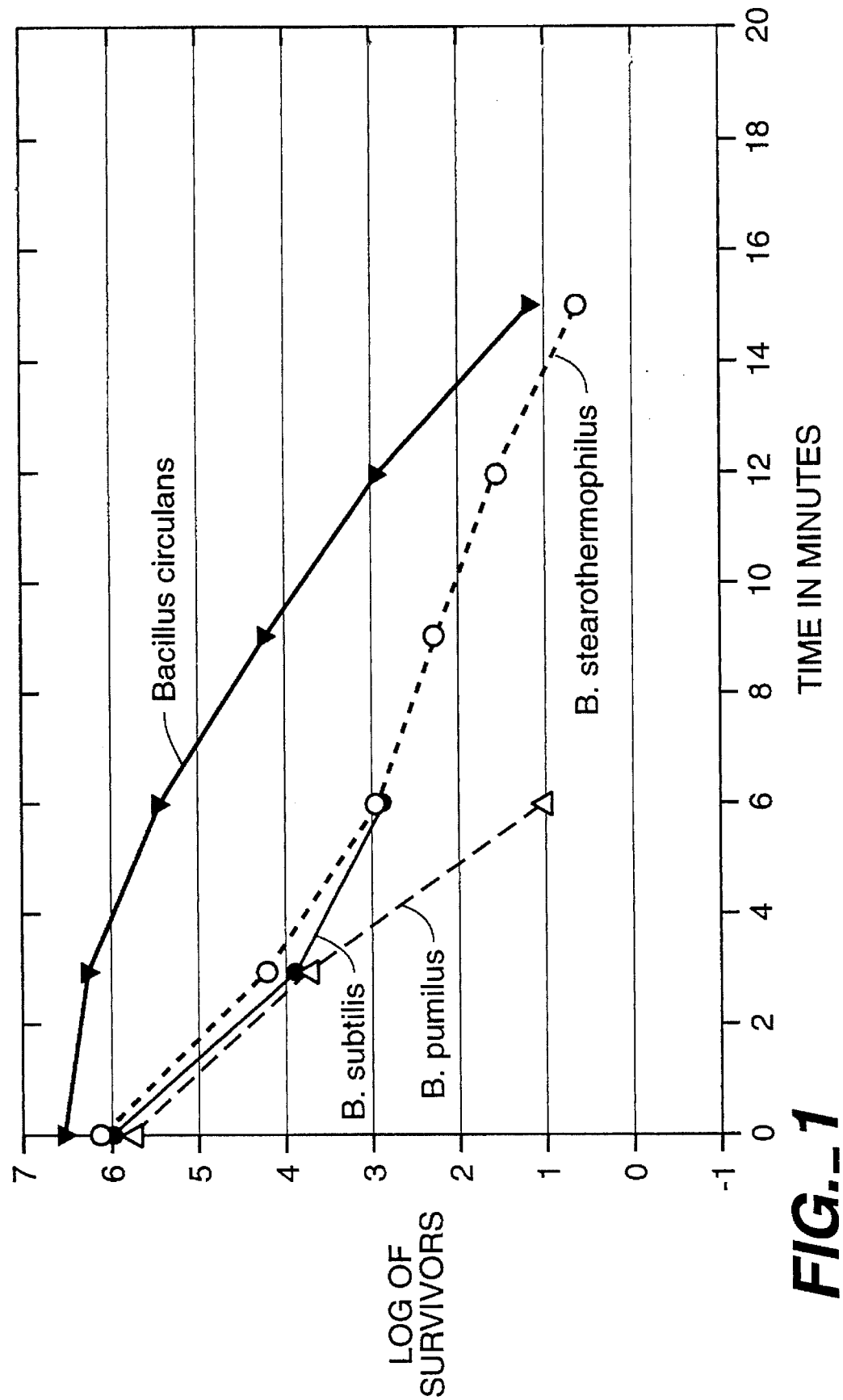
FIG._1

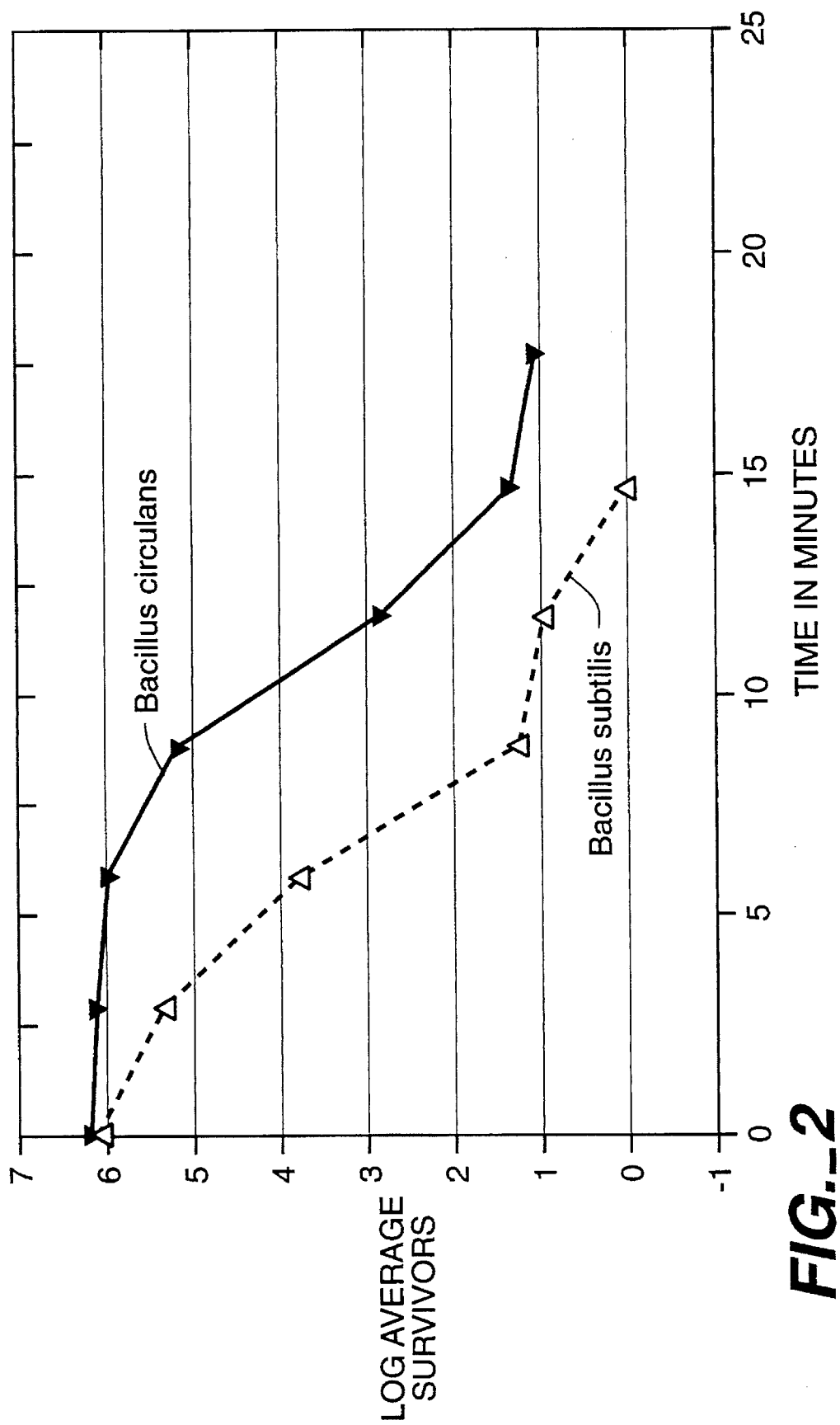
FIG._2

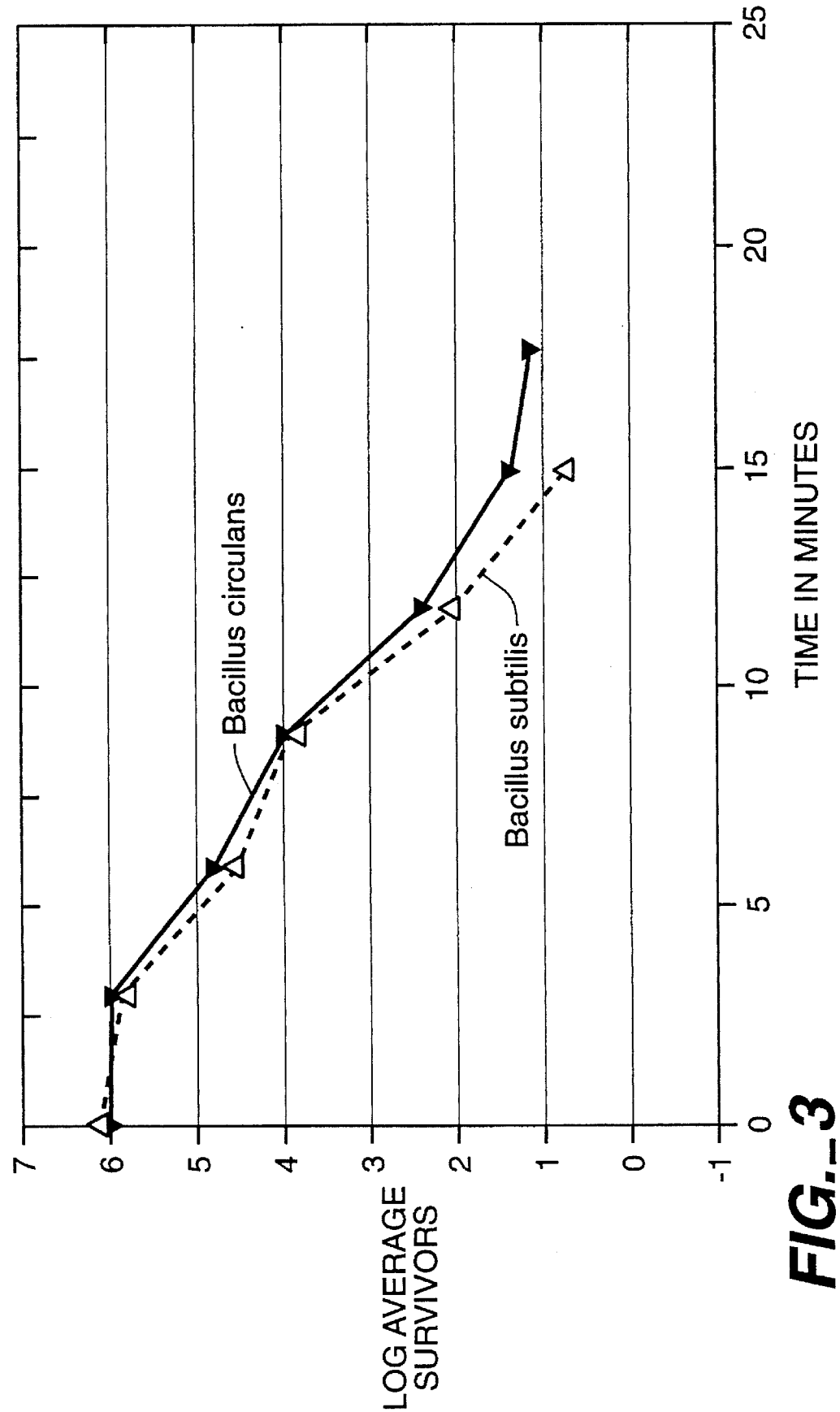
FIG._3

BACILLUS CIRCULANS BASED BIOLOGICAL INDICATOR FOR GASEOUS STERILANTS

FIELD OF THE INVENTION

The present invention generally involves biological indicators for gaseous sterilizing processes, and more particularly to the use of *Bacillus circulans* based biological indicators for gaseous oxidizing sterilants and sterilizing processes.

BACKGROUND OF THE INVENTION

The *U.S. Pharmacopeia XXII, Official Monograph*, pp. 1625–1626 begins by defining a biological indicator as "a characterized preparation of specific microorganisms resistant to a particular sterilization process. It is used to assist in the qualification of the physical operation of sterilization apparatus in the development and establishment of a validated sterilization process for a particular article, and the sterilization of equipment, materials, and packaging components for aseptic processing. It may also be used to monitor a sterilization cycle, once established, and periodically in the program to revalidate previously established and documented sterilization cycles. It is in one of two main forms, each of which incorporates a viable culture of a known species of microorganism. In one the spores are added to a carrier (disk or strip of filter paper, glass, or plastic) and packaged so as to maintain the integrity of the inoculated carrier but, when used appropriately in the individual immediate package, so as to allow the sterilizing agent to exert its effect. In the other, the spores are added to representative units of the lot to be sterilized (inoculated product) or to similar units (inoculated similar product)."

A bit later, the *Pharmacopeia*, at p. 1626, states: "A particular strain of microbial spores selected for use as a biological indicator and resistant to one sterilization process may not necessarily be suitable for other sterilization processes or even differing sterilizing conditions of the same mode of sterilization."

State and federal legislation are severely restricting the amount of hazardous gases, such as ethylene oxide (a carcinogen), in working environments for the use of systems or methods that produce toxic residues or exhaust products. Ethylene oxide has been widely used in hospitals and other areas of the health industry for sterilization processes.

The use of plasma to sterilize containers was suggested in U.S. Pat. No. 3,383,163. Plasma is an ionized body of gas which may be generated by the application of an electromagnetic field to gas. The ionized gas can contact microorganisms on the surfaces of the items to be sterilized and effectively destroy the microorganisms.

Two recently issued patents, of common assignment herewith, use oxidizing gases for sterilization. U.S. Pat. No. 5,084,239, issued Jan. 28, 1992, inventors Moulton et al., describes a process in which an antimicrobial agent treatment is alternated with a downstream plasma treatment. The antimicrobial agent may be peracetic acid vapor under reduced pressure conditions. U.S. Pat. No. 5,115,166, issued May 19, 1992, inventors Campbell et al., describes a plasma sterilizing apparatus and method where an article to be sterilized is exposed to active species made from a plasma. The plasma is generated from a mixture of oxygen; argon, helium, and/or nitrogen; and hydrogen, or with a mixture of air and hydrogen, supplemented by oxygen or nitrogen to give the desired ratios.

While such sterilizing processes involving oxidizing gases effectively kill organisms, including spores, without damage to the articles being sterilized and with no toxic residues or emissions presenting environmental safety hazards, monitoring the process has posed a challenge due to the reduced resistance of various commonly used biological indicator organisms to such processes. Further, *Bacillus stearothermophilus*, which is recognized as an organism useful in biological indicators for steam sterilizations, has been found to have a curvilinear response curve to oxidizing gas sterilization processes. This is disadvantageous because inactivation of an indicator organism must occur in a predictable manner. Thus, the number of viable indicator organisms in a biological indicator should decrease exponentially with exposure time to allow the sterilization process time to be adjusted with an appropriate safety margin. Under the right conditions, sterilization can approximate first order kinetics, and thus allow sterilization cycle times to be readily determined. Thus, better bacteriological indicators, particularly those suitable for gaseous oxidizing sterilants and sterilizing processes, would be useful.

SUMMARY OF THE INVENTION

Accordingly, it is an object of the present invention to provide a biological indicator with close to first order death kinetics in gas sterilizing processes once the sterilizing agent has penetrated the packaging and has reached a substantially steady, high concentration in the vicinity of the organism spores.

It is another object of the present invention to provide a biological indicator with more consistent and relatively stable resistance to oxidizing gas sterilizing processes.

These and other objects of the present invention are provided in one biological indicator embodiment comprising a selected number of viable organism spores contained in a package. The organism is *Bacillus circulans*. The package is impenetrable to microorganisms (that is, substantially bacteria impermeable), but has a portion having sufficient permeability to let a sterilizing amount of vapor come into contact with the spores during vapor sterilizing processes.

In another aspect of the present invention, a method for monitoring a sterilizing process is provided whereby a biological indicator including a selected number of viable *Bacillus circulans* spores are exposed to a sterilizing gas, such as an oxidizing gas. The biological indicator is then removed, and the carrier incubated. The number of surviving spores can be determined under spore growth conditions.

Biological indicators using *Bacillus circulans* as the organism are advantageous in gas sterilizing processes since the organism is considered non-pathogenic, is stable enough to provide a relatively long shelf life when packaged, is easy to grow so that sterility tests can be performed using common techniques and materials, and has been found to have a higher resistance and more stable resistant pattern when compared to prior art organisms such as *B. subtilis* and *B. stearothermophilus*.

BRIEF DESCRIPTION OF THE DRAWINGS

FIG. 1 graphically illustrates typical survivor curves for an embodiment of the invention and by comparison three other Bacillus organisms (*B. subtilis, B. stearothermophilus*, and *B. pumilus*) with the vertical axis being a logarithmic scale of survivors and the horizonal axis being time in minutes and where the process used was a synergistic exposure to two sterilants, one of which was peracetic acid vapor and the other of which was a plasma generated oxidizing gas mixture;

FIG. 2 compares survivor curves of *Bacillus circulans* and *Bacillus subtilis* in a sterilizing process where only peracetic acid vapor was used; and, FIG. 3 is similar to FIG. 2 but in a sterilizing process where only a plasma generated oxidizing gas mixture was used.

DETAILED DESCRIPTION OF THE PREFERRED EMBODIMENTS

Biological indicator embodiments of the invention must have spores of *Bacillus circulans* packaged to maintain integrity of the spores until the biological indicator is used for its intended purpose.

*Bacillus circulans* cultures are available, for example, from the American Type Culture Collection, 12301 Parklawn Drive, Rockville, Md. 20852. For example, among the *B. circulans* strains available are ATCC 61, ATCC 13403, and ATCC 21821, 21822 (subspecies *n. proteophilus* and *n. biotinicus*, respectively). The strain used to exemplify the present invention was obtained as ATCC 61.

Packages of the invention have at least a portion that is gas or vapor permeable, but bacteria impermeable. This portion may constitute the entire package, but more usually the package will be constructed of the portion and one or more other materials. The other material, when present, is usually gas and bacteria impermeable. Examples of impermeable materials suitable in forming part of the inventive packages include polyethylene, polypropylene, poly(vinyl chloride), and poly(ethylene terephthalate), usually in the form of film, sheet, or tube.

The portion that is permeable to gas or vapor, but impermeable to bacteria will typically be microporous with the volume average diameter of pores being in the range of from about 0.02 to about 0.5 μm. The words "gas" and "vapor" are used throughout as being substantially synonymous, but where "gas" may more clearly describe the active species generated from a plasma step. Suitable microporous materials include spunbonded polyethylene, spunbonded polypropylene, microporous polyethylene, and microporous polypropylene, usually in the form of film or sheet. Paper can also be used as the permeable portion for inventive embodiments. The thickness of the permeable material can vary, but usually will be in the range of from about 0.23 to about 0.65 mm. The gas or vapor permeable portion is configured so as to define at least one path for providing entry of sterilizing gas or active species from a plasma from the chamber in which sterilization is performed and into contact with the *Bacillus circulans* spores.

Packages of the invention can be formed with seams, joints, and seals made by conventional techniques, such as, for example, heat sealing and adhesive bonding. Examples of heat sealing include sealing through use of heated rollers, sealing through use of heated bars, radio frequency sealing, and ultrasonic sealing. Peelable seals based on pressure sensitive adhesives may also be used.

The package provides integrity for the enclosed organism during shelf life until use. Other microorganisms are prevented entry by the package as barrier, since other microorganisms could interfere with or confuse sterility determinations based on the expected number and type of organism spores. Thus, the organism spores within will be preserved in a condition so that subsequent laboratory analysis is meaningful and reliable.

Biological indicator embodiments of the invention preferably further include a carrier that is inoculated with the spores. As will be understood, the carrier is simply a means by which organism spores in a selected number are positioned within the package, and then subsequently analyzed for viability. Consequently, the carrier can vary widely in the choice of materials and shapes so long as the function as carrier is served.

It has been suggested that the type of product or carrier material inoculated can significantly affect the resistance of the biological indicator. The preferred filter paper carrier material has been shown to have excellent storage stability for embodiments of the invention. Preferred carriers are formed of materials such as filter paper, which can be readily macerated along with the carried spores if one wishes to perform survivor determinations.

The carrier, such as a preferred filter paper carrier, can be quite simply inoculated with spores by preparing an aqueous suspension with the desired spore concentration and pipetting aliquots onto the carrier. Thus, inoculation of carrier can be according to the USP XXII Bacteriostasis Test Method. Briefly, a suspension of *Bacillus circulans* spores in water is prepared so as to yield a desired number of spores per aliquot for inoculating a carrier such as filter paper.

Spores, rather than the vegetative form of the organism, are used because vegetative bacteria are known to be easily killed by sterilizing processes. Spores also have superior storage characteristics as they can remain in their dormant state for years. Thus, when sterilization of a standardized spore strain occurs from a sterilization process, such can provide a high degree of confidence that sterilization of bacterial strains in the sterilizing chamber has occurred. The *Bacillus circulans* spores of this invention may be placed into the package as a selected number as follows.

A selected number of spores are inoculated on the carrier. Before inoculating spores onto the carrier, a heat shock step is desirably performed. Heat shock is a sublethal thermal treatment given to spores to prepare the enzymatic reactions for germination. Thus, a preferred sequence is a heat shock step, cooling, diluting the liquid spore suspension, and then inoculating carriers. The following method can be used to prepare inoculated carriers and to perform a population count.

An inoculated disk is placed in a 10 ml dilution blank. Each disk is then macerated into a homogenous suspension and vortexed vigorously for a minimum of 15 seconds. Appropriate dilutions are then conducted and each is plated. TSA (Tryptic soy agar) may be used as the recovery (growth) medium. Between about 20 and 35 ml of agar is poured into each plate after the appropriate aliquot of the sample has been transferred. The plates are allowed to completely solidify, are inverted and incubated at 32°–37° C. for 24– 48 hours. Plates that contain between about 30 and 300 colony forming units are counted and the average population per disk is calculated.

Biological indicators of the invention can optionally include one or more desired additional elements, such as to indicate when the biological indicator has already been used. For example, such optional means can take the form of a marker, preferably a visual marker such as dye or color changeable ink. An optional such additional element can be interior the package or carried on an exterior surface. Another optional component can be where the package is flexible and includes spore growth medium in a frangible, sealed vial. This variation can be used to test for sterilization without having to remove the carrier. Illustrations of several such variations are discussed by U.S. Pat. No. 4,743,537, issued May 10, 1988; U.S. Pat. No. 4,717,661, issued Jan. 5, 1988; U.S. Pat. No. 3,661,717, issued May 9, 1972; and U.S. Pat. No. 3,440,144, issued Apr. 22, 1969, all incorporated herein by reference. Thus, after sterilization the biological indicator package can be bent or squeezed in order to rupture the vial. The carrier is then exposed to the released growth medium and can be incubated without the necessity of removing the carrier from the package in order to monitor the biological indicator for growth. A visual means for indicating growth, such as pH indicator dye, can be included.

The inventive biological indicators were developed for preferred use with a synergistic, two-step oxidizing gas sterilization process. However, biological indicators of the invention are broadly useful with other gaseous sterilants and other gaseous sterilizing processes.

In the first step of the particular two-step process for which the invention was developed, an oxidizing gas, typically peracetic acid vapor, is introduced as a sterilant. In the second step of the process, active species made in a plasma using a mixture of argon, oxygen, and hydrogen gases are passed through a gas distribution manifold to allow ion-electron recombination and fast relaxation processes to occur, and the oxidizing gas mixture is then introduced into the sterilizing chamber. U.S. Pat. No. 5,115,166 particularly describes the plasma generated gas mixture while U.S. Pat. No. 5,084,239 describes a two-step process, one step of which can use peracetic acid vapor as sterilant. Both patents are hereby incorporated herein by reference.

EXPERIMENTAL METHODOLOGY

Biological indicator embodiments of the invention were prepared as follows. Packages for the biological indicators were obtained from Baxter Laboratories as "Plastipeel Pouches." These pouches have an upper sheet of a gas permeable fabric of bound polyethylene fibers ("Tyvek"), which is already sealed on three edges and where the user seals the fourth edge, after insertion of the carrier, to a lower sheet of impermeable clear polyester film ("Mylar"). Filter paper disks (¼ inch diameter Schleicher & Schuell 740E) were used as the carriers. Each disk was inoculated with $10^6$ spores of viable organism. For comparative survivor curve experiments, each pouch contained two paper carriers, one with *Bacillus circulans* spores and the other with the organism for comparison, such as *Bacillus subtilis*. In comparing survivor curves and performing fraction negative analyses for spores of *Bacillus subtilis* and others with *Bacillus circulans*, heat seals were used to create separate compartments.

Exposure intervals for exposure to the sterilizing gas were chosen, and the biological indicators placed into a Plazlyte sterilizer (AbTox). Such an apparatus is substantially as described in U.S. Pat. Nos. 5,115,166 and 5,084,239. The biological indicators were exposed to only a peracetic acid cycle, only a plasma cycle, or both cycles for the selected exposure required time intervals. The amount of peracetic acid vapor for a cycle used was approximately 2 mg/l, and the vapor was obtained by evaporating a peracetic acid solution. Thus, in addition to what is believed to be the primary gaseous oxidizing species of peracetic acid, the vapor also includes hydrogen peroxide and acetic acid (and water). The feed gas for the plasma generated gaseous mixture was argon, oxygen, and hydrogen, which was prepared with about 91.4% argon, 3.8% hydrogen, and 4.7% oxygen and for a cycle was flowed at a volume of about 5.5 standard l/min. The combined treatment (both sterilants) used peracetic acid vapor exposure for a time interval double that (and preceding) treatment with the plasma generated gas mixture. For example, the three minute exposure time involved exposing the carriers to peracetic acid vapor for two minutes and then subjecting them to the plasma process for one minute.

After exposing the biological indicators to the sterilizing gas treatment (the wall temperature was maintained at about 95° F.) the indicators were removed and tested for sterility.

Each pouch was cut open and each carrier was aseptically transferred to labelled, individual grind tubes. Each tube was vortexed until the carriers were macerated. Each macerated carrier was serially diluted using standard plate count techniques. The number of surviving spores (if any) were determined under spore growth conditions.

Survivor curves with the number of surviving spores being determined as a function of exposing step time were generated. D-values for the separate components were calculated using linear regression analysis. D-values (decimal reduction) are the time required at a given set of exposure conditions to reduce a specific population by 90%, and are the negative reciprocal of the slope of the line fitted to the graph of the logarithm of the number of survivors versus time.

Following the experimental methodology just described, data for biological indicator embodiments of the invention and comparative data were determined, as described below.

EXAMPLE 1

Using peracetic acid vapor as the sole sterilant, survivor curves and fraction negative analyses were generated for spores of *Bacillus subtilis* and *Bacillus circulans*. Exposure times for enumeration were 3, 6, 9, 12, 15, and 18 minutes (and for fraction negative testing, exposure times were 9, 12, 15, 18, 21, and 24 minutes. After exposure, each biological indicator was tested for population or sterility and an additional three unexposed carriers from each microorganism were enumerated as positive controls. Table 1 sets out the average data from triplicate such experiments.

TABLE 1

|    | Inventive Embodiment (*Bacillus circulans*) | Comparative (*Bacillus subtilis*) |
|----|---------------------------------------------|-----------------------------------|
| 0  | 6.21                                        | 6.04                              |
| 3  | 6.12                                        | 5.38                              |
| 6  | 6.00                                        | 3.78                              |
| 9  | 5.19                                        | 1.34                              |
| 12 | 2.82                                        | 1.03                              |
| 15 | 1.34                                        | 0.03                              |
| 18 | 1.10                                        | −0.32                             |

D-values with peracetic acid vapor phase only were 3.0 minutes for *B. circulans* (and 2.2 minutes for peracetic acid vapor phase with *B. subtilis*).

The data of Table 1 is plotted in FIG. 2. These data show that *Bacillus circulans* is as resistant to peracetic acid vapor as *B. subtilis*, but with a major difference being the lag factor exhibited for *Bacillus circulans* at the shorter process exposures.

EXAMPLE 2

Another experiment similar to that described for Example 1 was performed (in triplicate), but where the inventive biological indicator embodiments and the comparative indicators were exposed to the plasma phase cycle only. The data from this experiment are set out in Table 2.

TABLE 2

|    | Inventive Embodiment (*Bacillus circulans*) | Comparative (*Bacillus subtilis*) |
|----|---------------------------------------------|-----------------------------------|
| 0  | 6.00                                        | 6.12                              |
| 3  | 5.96                                        | 5.86                              |
| 6  | 4.82                                        | 4.64                              |
| 9  | 3.93                                        | 3.88                              |
| 12 | 2.41                                        | 2.06                              |
| 15 | 1.44                                        | 0.79                              |
| 18 | 1.18                                        | 0.70                              |

These data are plotted by FIG. 3 and demonstrate that *Bacillus circulans* is as resistant to the plasma processing cycle as *Bacillus subtilis*.

EXAMPLE 3

Another experiment was performed (in triplicate) in a similar manner to Examples 1 and 2 but where a peracetic acid vapor cycle was conducted followed by the plasma generated, oxidizing gas mixture cycle. In addition, comparison was made with two more organisms. Table 3 sets out these data while FIG. 1 graphically illustrates the typical survivor curve analysis of an inventive embodiment when compared to three other organisms.

TABLE 3

|    | Inventive Embodiment *B. circulans* | Comparative *B. subtilis* | *B. stearothermophilus* | *B. pumilus* |
|----|-------------------------------------|---------------------------|-------------------------|--------------|
| 0  | 6.54                                | 6.05                      | 6.16                    | 5.79         |
| 3  | 6.27                                | 3.87                      | 4.19                    | 3.77         |
| 6  | 5.49                                | 2.85                      | 2.92                    | 1            |
| 9  | 4.22                                |                           | 2.24                    |              |
| 12 | 2.91                                |                           | 1.56                    |              |
| 15 | 1.16                                |                           | 0.58                    |              |

D-values for *B. circulans* in the combined process (peracetic acid vapor cycle followed by plasma phase cycle) were in the range of 1.7 to 2.4 minutes.

EXAMPLE 4

The population and resistance stability of biological indicator embodiments of the invention were investigated, since a known, predictable, stable level of resistance is important to be maintained over an adequate shelf life. Table 4 sets out the data taken from the biological indicator stability evaluations over an eight month storage time (ambient conditions).

TABLE 4

| Lot Number | Storage Time (Month) | Spore Count* × $10^6$ |
|------------|----------------------|------------------------|
| 1          | 0                    |                        |
|            | 2                    | 2.0                    |
|            | 5                    | 1.9                    |
|            | 6                    | 2.2                    |
|            | 8                    | 2.0                    |
| 2          | 0                    |                        |
|            | 2                    | 2.1                    |
|            | 5                    | 1.8                    |
|            | 6                    | 2.6                    |
|            | 8                    | 2.3                    |

TABLE 4-continued

| Lot Number | Storage Time (Month) | Spore Count* × $10^6$ |
|------------|----------------------|------------------------|
| 3          | 0                    |                        |
|            | 2                    | 2.0                    |
|            | 5                    | 1.6                    |
|            | 6                    | 2.1                    |
|            | 8                    | 1.6                    |

*Reported population represents the averaged counts derived from a minimum quantity of six (6) individual BI's, each plated in triplicate.

This data indicates the ambient temperature storage stability of the *B. circulans* spores dried on paper carriers demonstrates storage stability for an eight month or longer product expiration date.

Biological indicator embodiments of the invention are contemplated to be an integral part of oxidizing gas sterilization cycle validation and routine monitoring programs and can be used quantitatively to demonstrate that sterilization has been achieved. The known population and resistance levels of inventive embodiments can be used to give sterilization assurances to any predetermined probability, and provide a known, predictable, stable level of resistance over a reasonable ambient temperature shelf life.

It is to be understood that while the invention has been described above in conjunction with preferred specific embodiments, the description and examples are intended to illustrate and not limit the scope of the invention, which is defined by the scope of the appended claims.

It is claimed:

1. A method for monitoring a sterilizing process, comprising:

disposing a biological indicator in a sterilizing chamber, the biological indicator including a selected number of viable *Bacillus circulans* spores inoculated onto a carrier;

exposing the biological indicator to at least one sterilant being in gaseous form;

removing the biological indicator from the sterilizing chamber; analyzing or having the carrier analyzed for spore growth wherein the analysis is by incubating the carrier spores under spore growth conditions; and determining a number of surviving spores, if any.

2. The method as in claim 1 wherein the at least one sterilant in gaseous form comprises an oxidizing gas.

3. The method as in claim 1 wherein the at least one sterilant in gaseous form comprises peracetic acid vapor, hydrogen peroxide vapor or a mixture of peracetic acid and hydrogen peroxide vapors, and another sterilant that includes a plasma generated from oxygen or a gas mixture of oxygen and one or more of argon, helium, nitrogen, and hydrogen.

4. The method as in claim 1 wherein the sterilizing chamber is evacuated before the exposing step.

5. The method of in claim 4 wherein the evacuation is to a reduced pressure of from about 0.1 to about 10 torr.

6. The method as in claim 1 wherein the at least one sterilant comprises peracetic acid vapor.

7. The method as in claim 1 wherein the at least one sterilant comprises hydrogen peroxide vapor.

8. The method as in claim 1 wherein the at least one sterilant comprises a mixture of peracetic acid and hydrogen peroxide vapors.

9. The method as in claim 1 wherein the at least one sterilant comprises a plasma generated from oxygen or a gas mixture of oxygen and one or more of argon, helium, nitrogen, and hydrogen.

10. The method as in claim 1 wherein the exposing step further comprises further exposing to a second sterilant after exposure to the at least one sterilant.

11. The method as in claim 10 wherein the at least one sterilant comprises peracetic acid vapor, hydrogen peroxide vapor, or a mixture of peracetic acid and hydrogen peroxide vapors.

12. The method as in claim 10 wherein the second sterilant comprises a plasma generated from oxygen or a gas mixture of oxygen and one or more of argon, helium, nitrogen, and hydrogen.

13. The method as in claim 1 wherein the at least one sterilant comprises an antimicrobial vapor and another sterilant derived from a plasma.

* * * * *